United States Patent
Boettcher-Wilmes

(10) Patent No.: US 10,912,446 B2
(45) Date of Patent: Feb. 9, 2021

(54) MONITORING OF THE CONNECTION OF FLUID LINES TO SURGICAL INSTRUMENTS

(71) Applicant: OLYMPUS WINTER & IBE GMBH, Hamburg (DE)

(72) Inventor: Marius Boettcher-Wilmes, Hamburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 412 days.

(21) Appl. No.: 15/727,144

(22) Filed: Oct. 6, 2017

(65) Prior Publication Data

US 2018/0028051 A1 Feb. 1, 2018

Related U.S. Application Data

(63) Continuation of application No. PCT/EP2016/055983, filed on Mar. 18, 2016.

(30) Foreign Application Priority Data

Apr. 8, 2015 (DE) .................... 10 2015 206 267

(51) Int. Cl.
*A61B 1/00* (2006.01)
*A61B 1/12* (2006.01)

(52) U.S. Cl.
CPC ...... *A61B 1/00114* (2013.01); *A61B 1/00119* (2013.01); *A61B 1/121* (2013.01)

(58) Field of Classification Search
CPC .. A61B 1/121; A61B 1/00119; A61B 1/00114
See application file for complete search history.

(56) References Cited

U.S. PATENT DOCUMENTS

| 4,894,495 | A | 1/1990 | Toda |
| 5,469,841 | A | 11/1995 | Kobayashi et al. |
| 2005/0209507 | A1 | 9/2005 | Suzuki et al. |
| 2007/0100203 | A1 | 5/2007 | Jackson et al. |
| 2007/0185385 | A1 | 8/2007 | Noguchi et al. |

(Continued)

FOREIGN PATENT DOCUMENTS

| DE | 37 08 131 A1 | 9/1987 |
| DE | 10 2012 020 934 A1 | 4/2014 |

(Continued)

OTHER PUBLICATIONS

International Search Report dated Jun. 2, 2016 received in PCT/EP2016/055983.

(Continued)

*Primary Examiner* — Sean E Conley
(74) *Attorney, Agent, or Firm* — Scully, Scott, Murphy & Presser, P.C.

(57) ABSTRACT

A monitoring system for reprocessing a surgical instrument, where the monitoring system includes: a fluid line provided for supplying a fluid to the surgical instrument, the fluid line being configured to be connected to the surgical instrument; and a fluid line connection for connecting the fluid line to the surgical instrument; wherein the fluid line connection is configured to close an electrical contact in the case of a functional connection of the fluid line to the surgical instrument.

5 Claims, 1 Drawing Sheet

(56) References Cited

U.S. PATENT DOCUMENTS

| | | |
|---|---|---|
| 2009/0158539 A1 | 6/2009 | Onishi et al. |
| 2009/0217956 A1 | 9/2009 | Noguchi et al. |
| 2013/0252461 A1* | 9/2013 | Gross .................. H01R 13/005 |
| | | 439/577 |
| 2015/0216608 A1 | 8/2015 | Eschborn et al. |

FOREIGN PATENT DOCUMENTS

| | | |
|---|---|---|
| DE | 10 2012 218 811 A1 | 4/2014 |
| EP | 1 728 465 A1 | 12/2006 |
| EP | 1 767 140 A1 | 3/2007 |
| EP | 1 779 769 A2 | 5/2007 |
| EP | 1 902 670 A1 | 3/2008 |
| EP | 2 080 486 A2 | 7/2009 |
| JP | 2009-131327 A | 6/2009 |
| WO | 03/067138 A1 | 8/2003 |

OTHER PUBLICATIONS

Olympus—ETD 4—reliable handling of flow control—company publication, 4 pages, retrieved from Internet on Mar. 22, 2016.
Wassenburg Medical Devices—Pentax Medical—product brochure of Aug. 2013—company publication, 2 pages.
Getinge—Getinge Aer range—product brochure of Aug. 2011—company publication, 28 pages.

* cited by examiner

MONITORING OF THE CONNECTION OF FLUID LINES TO SURGICAL INSTRUMENTS

CROSS-REFERENCE TO RELATED APPLICATION

The present application is a continuation of PCT/EP2016/055983 filed on Mar. 18, 2016, which is based upon and claims the benefit to DE 10 2015 206 267.8 filed on Apr. 8, 2015, the entire contents of each of which are incorporated herein by reference.

BACKGROUND

Field

The present application relates to a monitoring system for reprocessing surgical instruments, wherein a fluid line is provided for supplying a fluid to the surgical instrument, which fluid line is connectable or connected to the surgical instrument, wherein the fluid line has a fluid line connection for connecting to the surgical instrument. The present application further relates to a method for connecting a surgical instrument to at least one fluid line which, during the reprocessing of the surgical instrument, conducts fluid to the surgical instrument or conducts fluid away from the surgical instrument, wherein the at least one fluid line is connected to at least one connection of the surgical instrument. The present application further relates to a method for operating a reprocessing apparatus for reprocessing a surgical instrument.

Prior Art

A reprocessing apparatus and a method for operating a corresponding reprocessing apparatus or respectively a reprocessing system is disclosed in DE 10 2012 218 811 A1. In this case, corresponding baskets, which may be introduced into a reprocessing apparatus, are loaded with surgical instruments, wherein fluid lines are connected to instrument connections of the surgical instrument. In order to permit a reprocessing of the surgical instruments corresponding channels of the surgical instrument are rinsed with fluid.

In the reprocessing of surgical instruments, such as for example endoscopes, it is known to undertake a tightness test when rinsing the internal channels of surgical instruments, so that in the case of an incorrectly connected instrument adapter or respectively an incorrectly connected fluid line, an interruption to the process occurs during the reprocessing of the surgical instrument. In order to carry out the tightness test, for example in the case of an incorrectly connected adapter, a certain level of excess pressure may be created and it may be observed how the drop in pressure progresses within a test period. When rinsing the internal channels, for identifying an incorrectly connected adapter or respectively an incorrectly connected fluid line, water is generally passed in the reprocessing apparatus through the surgical instrument and by a corresponding measurement of water pressures or water quantities it is identified whether a connection is faulty. In this case, the rinsing water has to be initially pumped off before the connection may be corrected. This process is relatively time-consuming.

SUMMARY

It is the object to provide a very rapid and efficient means of providing a correct connection of fluid lines to a surgical instrument.

Such object can be achieved by a monitoring system for reprocessing surgical instruments, wherein a fluid line is provided for supplying a fluid to the surgical instrument, which fluid line is connectable or connected to the surgical instrument, wherein the fluid line has a fluid line connection for connecting the fluid line to the surgical instrument, which is developed by the fluid line connection closing an electrical contact in the case of a functional connection to the surgical instrument.

"Functional connection" within the scope of this disclosure is understood as a fluid-tight connection, by which a reliable rinsing and namely leak-free rinsing of the surgical instrument is permitted, in particular a lumen or a channel or a plurality of channels in the surgical instrument. A "functional connection" is also understood as a connection in which a defined or predeterminable leakage is provided. Via this leakage, external surfaces of the connection may also be acted upon by fluid, such as for example a disinfecting solution. As a result, a disinfection is possible over the entire surface. A functional connection is present, for example, when it is ensured that the connection of the fluid line to the surgical instrument remains securely connected, even in the case of the highest possible pressures used during the rinsing by means of a fluid.

This can be ensured by an electrical contact being closed only in the case of a functional connection of the fluid line connection to the surgical instrument, which may serve to identify to an operator that a functional connection is present.

Within the scope of this disclosure, "closing an electrical contact" is understood that an electrical current is able to flow via the electrical contact. The electrical contact may be permitted, for example, by a switch such as a push button switch which is arranged on the fluid line connection or, for example, by a contact being closed between an external surface of the fluid line, which is electrically conductive, and an external surface of the surgical instrument or an instrument connection of the surgical instrument which is at least partially conductive.

When closing the electrical contact a signal which is detectable by an operator can be generated. The detectable signal may be a tone or an optical image, such as for example an optical image on a monitor or a display apparatus of the monitoring system. Alternatively or additionally, a movement such as for example a vibration may be produced.

An electrical connection can be provided from the electrical contact, such as via the fluid line, to a control apparatus of the monitoring system. As a result, in a simple manner, the control apparatus may serve to generate signals which are detectable by the operator.

The fluid line can be a hose.

If the electrical connection is or comprises a conductive strand or a conductive layer arranged in or on the fluid line, a user-friendly monitoring system can be provided. The electrically conductive strand or the electrically conductive layer can be metal. Two conductive layers or conductive strands may also be provided in or on the fluid line in order to permit a circuit from the control apparatus through the fluid line to the connection and back. The conductive strand or the electrically conductive layer can be coated at least partially with an electrically non-conductive material.

Alternatively, only one electrical line or respectively electrical connection may be provided and thus via an earth connection or an earth lead, for example, a corresponding current may be discharged via the surgical instrument.

The fluid can be a liquid.

The fluid line connection can have an electrically conductive contact surface on the front face, the contact surface in the case of a functional connection of the fluid line connection to the surgical instrument can be in electrical contact with an electrically conductive surface of the surgical instrument. In this case, two electrically conductive contact surfaces can be provided on the front face of the fluid line connection, which by contact with the surgical instrument are to be electrically connected together or are electrically connected together.

A reprocessing apparatus for reprocessing surgical instruments can comprise the above monitoring system.

Such object can also be achieved by a method for connecting a surgical instrument to at least one fluid line which, when reprocessing the surgical instrument, conducts fluid to the surgical instrument or conducts fluid away from the surgical instrument, wherein the at least one fluid line is connected to at least one connection of the surgical instrument, wherein by means of a control apparatus it is monitored whether a functional connection of the at least one fluid line to the at least one connection of the surgical instrument is present, whereupon the control apparatus generates a signal.

In this case it is established whether a functional connection of the at least one fluid line to the at least one connection of the surgical instrument is present, for example by switching a switch, which is switched on in a final mounting position of a fluid line after it has been connected to the surgical instrument or due to a contact of electrical lines, so that in this manner an electrical contact is also closed in the case of a functional connection of the at least one fluid line to the at least one connection of the surgical instrument. The control apparatus can comprise a testing apparatus or is a testing apparatus.

An error message can be generated in the case of a non-functional connection of the fluid line to the surgical instrument. For example, the error message may be produced when a predeterminable time has passed after an operator has initiated the connection or respectively the connecting process without it resulting in a functional connection of the fluid line. It may also be provided that the control apparatus starts a computer program or a waiting loop as soon as an operator inputs that a connection is now desired from a surgical instrument to a fluid line or to a plurality of fluid lines. The program in this case may provide the means of predetermining instructions to the operator for the correct connection of fluid lines or a fluid line to the surgical instrument. The operator may then successively connect the fluid lines and after each connection of a fluid line, for example, a test button may be actuated by the operator or an initializing command may be input in order to monitor whether a functional connection is present.

It may also be provided that at the moment when the surgical instrument is conveyed into the region of a loading station, it is automatically identified which surgical instrument is present, so that for the monitoring system it is clear which fluid connections have to be connected. This may be brought to the attention of an operator by the monitoring system, for example via the display on a display unit. To this end, the surgical instrument may be provided with identifying features, such as for example an RFID chip, via which a clear identification of the surgical instrument is possible. This loading station may be an apparatus which is spatially separate from a reprocessing apparatus and serves, for example, to load baskets with surgical instruments which are to be reprocessed, for introducing into a reprocessing apparatus in a convenient and secure manner.

The signal can be a confirmation signal which is generated by a control apparatus, such as a reprocessing apparatus, such as when an electrical contact provided on a fluid line connection is closed. The confirmation signal may, for example, be a tone.

For connecting a plurality of fluid lines to the surgical instrument an image of the connections to be made can be provided on a display apparatus, such as of the monitoring system, wherein after the operator has acknowledged a connection which has been made it is monitored by the control apparatus whether the connection which has been made is functional. In the event that the connection is not functional, an error message which is assigned to the connection which has been made can be generated. The error message may be an optical display or even an acoustic signal.

The faulty connection can be displayed on the display apparatus.

Additionally, it is provided to carry out a method for operating a reprocessing apparatus for reprocessing a surgical instrument using an aforementioned method for connecting a surgical instrument to at least one fluid line, wherein a reprocessing of the surgical instrument is initiated only in the case of a functional connection of all fluid lines. When reprocessing the surgical instrument, in particular a fluid, such as a liquid, is conveyed by the fluid line or the fluid lines.

During the reprocessing of the surgical instrument or respectively during the operation of the reprocessing apparatus it can be monitored whether the connection or the connections of the fluid lines remains or remain functional.

By means of the provided monitoring system and/or reprocessing apparatus, it is possible to identify an incorrectly connected adapter or respectively an incorrectly connected fluid line to a surgical instrument immediately when connecting the fluid line to the surgical instrument. To this end, contacts, for example front face contacts, are provided on the end portions of the fluid line or respectively the fluid lines or the fluid line connections. With a correctly connected fluid line connection, the contact which has been made is then electrically closed. The electrically closed contact is represented, for example by means of the control apparatus, by a combination of acoustic and visual feedback.

Immediately when connecting the fluid line connection or respectively the fluid line to the surgical instrument, the operator can receive, by means of the control apparatus, an acoustic signal, for example, a single tone in the case of a correct connection and a repeated tone in the case of a faulty connection. In this case, it is not necessary for the operator to look away from the fluid line connection.

Additionally, it is also expedient to represent visual feedback, for example, on a display apparatus, for example a green check mark may be provided for each correctly connected fluid line connection or respectively each correctly connected fluid line on the display apparatus. Accordingly, for each incorrectly connected fluid line or respectively each incorrectly connected fluid line connection a red cross may be shown.

Thus before the actual start of a reprocessing process, the operator receives an acknowledgement as to whether the inserted surgical instrument is correctly connected.

The functionality of the monitoring system or respectively the reprocessing apparatus can be developed by an automatic instrument identification. In this case, the monitoring system or respectively the reprocessing apparatus identifies the surgical instrument and, as a result, may show the correct fluid line connections on a display apparatus graphically or in the form of a list. The successful or faulty connection for each individual fluid line connection or respectively for each individual fluid line may be visualized on this image on the display apparatus.

The identification of whether the fluid line or respectively the fluid line connections are correctly connected may be undertaken as a previous process step before an actual reprocessing process. In this previous process step, for example, the front surface contacts of the fluid lines or respectively the fluid line connection may be activated via the control apparatus. By a subsequent deactivation of the contacts it is possible to eliminate the occurrence of a faulty detection due to water which correspondingly enters or circulates during the reprocessing.

BRIEF DESCRIPTION OF THE DRAWINGS

Further features are disclosed from the description of embodiments, together with the claims and the accompanying drawings. Embodiments may fulfill individual features or a combination of a plurality of features.

The embodiments are described hereinafter without limiting the general inventive idea using exemplary embodiments with reference to the drawings, wherein relative to all of the details, which are not shown in more detail in the text, reference is expressly made to the drawings, in which.

DETAILED DESCRIPTION

Figure 1:
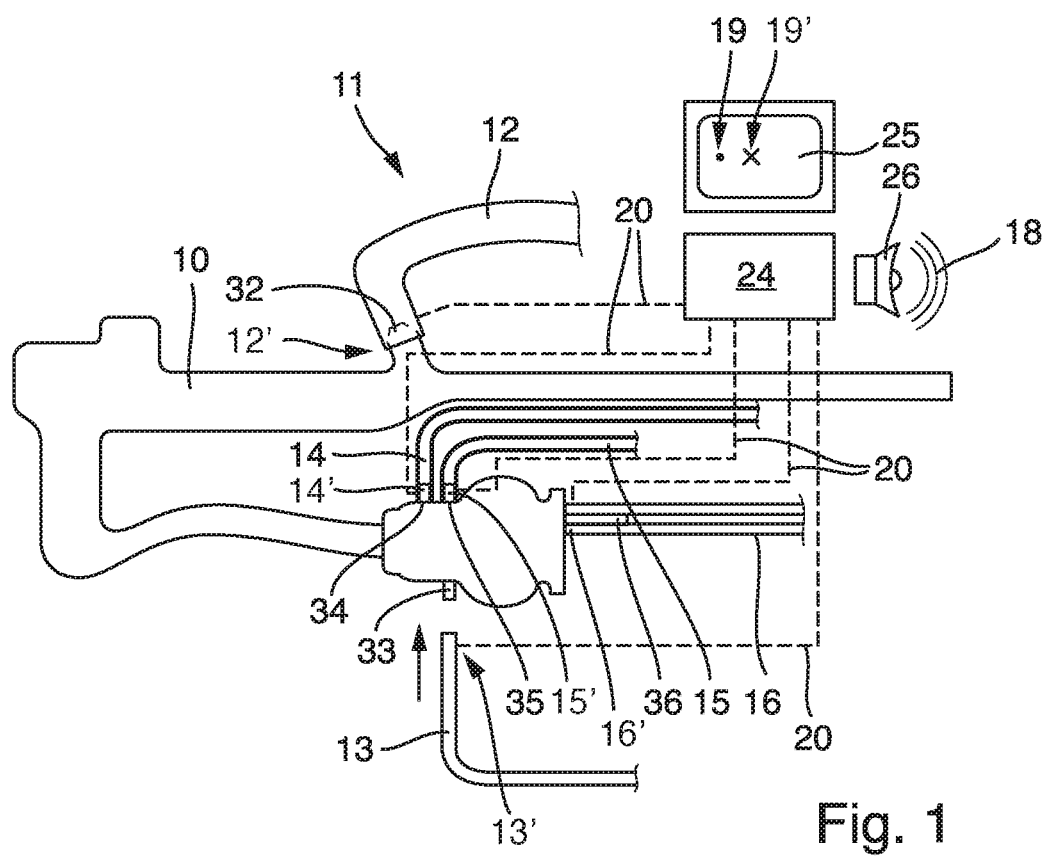
FIG. 1 illustrates a schematic view of a monitoring system.

In the drawings, the same or similar elements and/or parts are provided in each case with the same reference numerals, so that in each case a further description is dispensed with.

FIG. 1 shows schematically a monitoring system 11 for the connection of a surgical instrument 10 to fluid lines 12-16.

Surgical instruments, such as for example endoscopes, have channels or lumens which have to be cleaned and disinfected after the use of the surgical instrument. To this end, these instruments are typically placed into a reprocessing apparatus. In the reprocessing apparatus a cleaning fluid is passed from outside onto the surgical instrument and additionally the corresponding channels or respectively lumens 23, amongst other things, are rinsed with a cleaning fluid.

In order to be able to undertake correct cleaning, i.e. complete cleaning and disinfecting, i.e. reprocessing the surgical instrument, it is necessary that the fluid lines 12-16 with the fluid line connections 12'-16' on the front face or respectively end face are connected to the instrument connections 32-36. The connection may be leakage free. Alternatively, a connection may be provided with a defined leakage.

Figure 2:
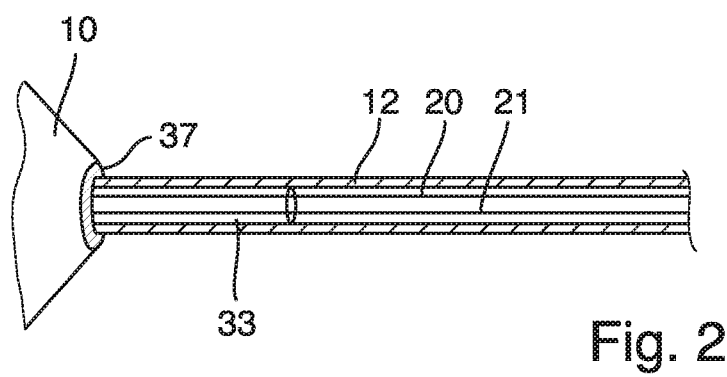
FIG. 2 illustrates a schematic view of a connection of a fluid line to a surgical instrument in a schematic detailed view.
Figure 3:
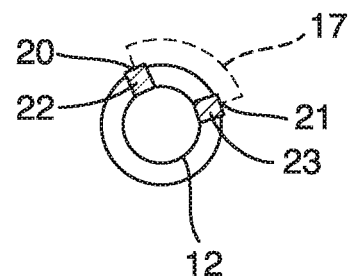
FIG. 3 illustrates a schematic sectional view through a schematic front view of a fluid line.

In order to be able to undertake a reprocessing in an efficient manner, it is provided, when providing the surgical instrument or respectively instrument connections 32-36 with the fluid line connections 12'-16' or respectively with the fluid line 12-16, to monitor whether the connections are functional, for example, such that they have been completely correctly implemented. To this end, in the case of a functional connection, an electrical contact is closed. The electrical contact may be closed, for example as shown in FIG. 2, by two electrical lines 20, 21 which are arranged on the outer face of the fluid line 12, as shown in FIG. 3, extending as far as the front face and in each case forming an end contact surface 22 or respectively 23 at that point, and which are brought into electrical contact with an electrically conductive surface 37 of the surgical instrument 10. As a result, an electrical current may be passed from a controller 24, such as a computer or CPU, via the closed electrical contact between the end contact surfaces 22 and 23 and the electrically conductive surface 37 of the endoscope 10, whereby it may be established that a correspondingly functional connection is present. Alternatively, a resistance between the electrical lines 20 and 21 may be measured, wherein when a predeterminable value for the resistance is fallen below, a functional connection is assumed.

This type of electrical contact is just one type of many conceivable options. Alternatively, a switch which is arranged in the fluid line or on the fluid line and is closed in the case of contact with an end surface of the surgical instrument may also be provided. Alternatively, it may also be provided to furnish the fluid line with a fluid line connection, which may be connected in the manner of a bayonet connection to an instrument connection of the surgical instrument 10, and to this end closes an electrical contact only with a correspondingly complete rotation of the bayonet in the object.

In FIG. 1 it is shown entirely schematically and generally how corresponding electrical lines 20 are passed from the connection between the fluid line and the surgical instrument to a control apparatus 24. Additionally, for example, the fluid line 13 is still separate from the instrument connection 33. The fluid line 13 is intended to be pushed further in the direction of the arrow onto the instrument connection 33. The corresponding fluid lines 12-16 are shown only partially in FIGS. 1 and 2.

With a corresponding functional connection of the respective fluid line connection to the surgical instrument or respectively the respective instrument connection 32-36 the control apparatus is able to generate an acoustic signal 18 via a loudspeaker 26 and/or generate a visual signal 19 or 19' on the display apparatus 25, which display to an operator whether the connection is functional or not.

The fluid lines 12-16 may be hoses, such as flexible fluid lines.

In FIG. 3 it is shown schematically how an electrical contact 17 is produced. This electrical contact 17 is produced via the end contact surfaces 22 and 23 when said contact surfaces come into contact with an electrically conductive surface. In this case, an electrical contact 17 is closed, which is transmitted to the control apparatus 24 via the corresponding electrical lines 20 or respectively 21 connected to the end contact surfaces 22 and 23.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

10 Surgical instrument
11 Monitoring system 12, 13, 14, 15, 16 Fluid line
12', 13', 14', 15', 16' Fluid line connection
17 Electrical contact
18 Acoustic signal
19, 19' Visual signal
20, 21 Electrical line
22, 23 End contact surface
24 Control apparatus
25 Monitor
26 Loudspeaker
32, 33, 34, 35, 36 Instrument connection
37 Electrically conductive surface

What is claimed is:

1. A monitoring system for reprocessing a surgical instrument, the monitoring system comprising:
   a fluid line provided for supplying a fluid to the surgical instrument, the fluid line being configured to be connected to the surgical instrument; and
   a fluid line connection for connecting the fluid line to the surgical instrument;
   wherein the fluid line connection is configured to close an electrical contact via an electrically conductive surface of the surgical instrument in the case of a functional connection of the fluid line to the surgical instrument; and
   the electrical contact comprises two electrical lines arranged on an outer face of the fluid line, the two electrical lines extending to a distal face of the fluid line to form first and second end contacts on the distal face, and
   the electrically conductive surface of the surgical instrument is configured to extend between and contact the first and second end contacts in the case of the functional connection of the fluid line to the surgical instrument.

2. The monitoring system according to claim 1, wherein when closing the first and second end contacts, a signal which is detectable by an operator is generated.

3. The monitoring system according to claim 1, further comprising an electrical connection provided from the first and second end contacts to a controller.

4. The monitoring system according to claim 1, wherein the fluid line is a hose.

5. The monitoring system according to claim 3, wherein the two electrical lines are one of a conductive strand or a conductive layer arranged on the outer face of the fluid line.

* * * * *